United States Patent [19]

Clementi et al.

[11] Patent Number: 5,712,701
[45] Date of Patent: Jan. 27, 1998

[54] SURFACE INSPECTION SYSTEM AND METHOD OF INSPECTING SURFACE OF WORKPIECE

[75] Inventors: Lee D. Clementi, Lake Wylie, S.C.; Michael E. Fossey, Charlotte, N.C.

[73] Assignee: ADE Optical Systems Corporation, Charlotte, N.C.

[21] Appl. No.: 399,962

[22] Filed: Mar. 6, 1995

[51] Int. Cl.$^6$ .................................................. G01N 21/88
[52] U.S. Cl. .......................................... 356/237; 356/343
[58] Field of Search ................................. 356/237, 446, 356/371, 342, 343

[56] References Cited

U.S. PATENT DOCUMENTS

| | | | |
|---|---|---|---|
| 4,314,763 | 2/1982 | Steigmeier et al. | 356/237 |
| 4,441,124 | 4/1984 | Heebner et al. | 350/237 |
| 4,505,585 | 3/1985 | Yoshikawa et al. | 356/237 |
| 4,508,450 | 4/1985 | Ohshima et al. | 356/237 |
| 4,541,712 | 9/1985 | Whitney . | |
| 4,630,276 | 12/1986 | Moran | 356/237 |
| 4,740,708 | 4/1988 | Batchelder | 356/237 |
| 4,875,780 | 10/1989 | Moran et al. | 356/237 |
| 4,889,998 | 12/1989 | Hagano et al. | 356/237 |
| 4,898,471 | 2/1990 | Stonestrom et al. | 356/237 |
| 4,902,131 | 2/1990 | Yamazaki et al. | 356/237 |
| 4,966,457 | 10/1990 | Hayano et al. . | |
| 5,067,798 | 11/1991 | Tomoyasu . | |
| 5,108,176 | 4/1992 | Malin et al. | 356/237 |
| 5,125,741 | 6/1992 | Okada et al. | 356/237 |
| 5,127,726 | 7/1992 | Moran | 356/237 |
| 5,135,303 | 8/1992 | Uto et al. | 356/237 |
| 5,177,559 | 1/1993 | Batchelder et al. | 356/237 |
| 5,189,481 | 2/1993 | Jann et al. | 350/237 |
| 5,191,466 | 3/1993 | Gross et al. . | |
| 5,461,474 | 10/1995 | Yoshii et al. | 356/237 |

FOREIGN PATENT DOCUMENTS

| | | |
|---|---|---|
| 42 27 593 A 1 | 2/1993 | Germany . |
| WO 94/12867 | 6/1994 | WIPO . |

OTHER PUBLICATIONS

Silicon Detector Corporation catalog (four pages) on Bi–Cell and Quadrant Silicon Detectors (1987).
Advanced Photonix, Inc. catalog, pp. 32–35, on Position Sensing Photodetectors, no date.

Primary Examiner—Richard A. Rosenberger
Attorney, Agent, or Firm—Bell, Seltzer, Park & Gibson, P.A.

[57] ABSTRACT

A surface inspection system and methods of inspecting a surface of a workpiece are provided for detecting particles, defects, or other surface characteristics in or on a surface of the workpiece. The surface inspection system preferably has a transporter arranged for transporting a workpiece along a material path and a rotator associated with the transporter and arranged for rotating a workpiece during translational travel along the material path. A scanner is positioned and arranged for scanning a surface of a workpiece during rotational and translational travel along the material path. The scanner preferably includes a light source arranged to generate a light beam therefrom and a deflector positioned to receive the light beam and arranged for deflecting the light beam along a predetermined scan path across a surface of the workpiece as the workpiece rotationally and translationally travels along the material path. A collector also is preferably arranged for collecting light specularly reflected and scattered from the surface of the workpiece during rotational and translational travel along the material path.

42 Claims, 4 Drawing Sheets fig. 1.

SURFACE INSPECTION SYSTEM AND METHOD OF INSPECTING SURFACE OF WORKPIECE

FIELD OF THE INVENTION

This invention relates to surface inspection systems and methods and, more particularly, to the inspection of articles or workpieces, such as silicon wafers, to detect the presence of particles, flaws, or defects on the surface of the articles.

BACKGROUND OF THE INVENTION

In the process of manufacturing an article or workpiece such as silicon or other semiconductor microchips, light is generally directed through a reticle mask to etch circuits into a silicon wafer. The presence of flaws, defects, dirt, dust, smudges or other foreign matter on the surfaces of the reticle mask or the silicon wafer is highly undesirable and adversely affects the resulting circuits. As a result, the reticles and the silicon wafers are necessarily inspected before use. One inspection technique is for a human inspector to visually examine each surface under intense light and magnification. Debris and defects that are smaller than can be visually detected by the human eye, however, impairs the resulting microchips or masks. Additionally, human judgment can vary widely even based on the same quality guidelines or standards for the inspection process.

Laser inspection systems therefore have been developed for inspecting the surface of articles such as silicon wafers to accurately detect small particles or defects. These laser inspection systems generally operate on the principle that a reflection of illuminating light from the surface of an article depends on the direction of the illumination relative to the wafer surface and the physical characteristics of the surface. These physical characteristics, for example, may include relatively smooth regions, undulating regions, roughness, particles, and/or other defects or flaws on the surface of the article. In these conventional laser inspection systems, light is both specularly reflected and scattered from the surface of an article. The specularly reflected light and the scattered light are both indicative of the presence of particles or defects on the surface of the article or the workpiece. The light specularly reflected from the surface, i.e., light channel, and the light scattered from the surface, i.e., dark channel, are each collected and separately relayed to photodetectors such as a photomultiplier tube ("PMT") or a charge coupled device ("CCD"). The light scattered from the surface of the article is also understood to include diffracted light.

Several laser inspection systems have been developed which provide various types of scanners and collectors for scanning a surface of an article or workpiece during translational travel and for collecting light reflected and scattered from the surface of the article. Examples of such systems may be seen in U.S. Pat. No. 4,630,276 by Moran titled "Compact Laser scanning System"; U.S. Pat. No. 5,108,176 by Malin et al. titled "Method Of Calibrating Scanners And Arrangement For Producing Defined Scattered Light Amplitudes"; and U.S. Pat. No. 5,127,726 by Moran titled "Method And Apparatus For Low Angle, High Resolution Surface Inspection."

The development of these laser inspection systems for detecting the presence of particle or defects on the surface of an article has also included various scanning techniques to provide increased information about the surface and particles being detected. Examples of several spiral scanning systems may be seen in U.S. Pat. No. 5,067,798 by Tomoyasu titled "Laser Beam Scanning System"; U.S. Pat. No. 5,135,303 by Uto et al. titled "Method Of And Apparatus For Inspecting Surface Defects"; U.S. Pat. No. 4,508,450 by Ohshima et al. titled "System For Checking Defects On A Flat Surface Of An Object"; U.S. Pat. No. 4,314,763 by Steigmeier et al. titled "Defect Detection System"; and U.S. Pat. No. 5,189,481 by Jann et al. titled "Particle Detector For Rough Surfaces." These inspection systems, however, illustrate only providing a spiral scan pattern to the surface of a silicon wafer. These systems limit the time required for inspecting the surface of an article and the amount of information provided during detection of the light reflected from the surface. These systems further are directed only to either high spatial resolution or high throughput for the surface inspection process.

With the foregoing in mind, it is an object of the present invention to provide a surface inspection system which compactly and efficiently scans and collects light reflected and scattered from a surface of a workpiece.

It is another object of the present invention to provide a surface inspection system that is efficient, has a relatively high spatial resolution, and has a relatively high throughput for the surface inspection process.

It is a further object of the present invention to provide a surface inspection system having high sensitivity to more readily identify and classify the condition of the surface of an article or a workpiece, including particles, defects, scratches, or flaws in and on a surface of a workpiece.

SUMMARY OF THE INVENTION

The above and other objects of the present invention are achieved by a surface inspection system and methods of inspecting a surface of a workpiece arranged for detecting particles, defects, or other surface characteristics in or on the surface of the workpiece. The surface inspection system preferably includes a scanner that scans across the surface of the workpiece along a predetermined, and preferably a relatively narrow, scan path during rotational and translational travel of the workpiece and a collector that has segmented optics for more accurately collecting reflected and scattered light from the surface of the workpiece. The surface inspection system thereby provides a relatively compact and highly efficient inspection system that is relatively easy to use, provides highly accurate results related to detected particles or defects on the surface thereof, and provides a high spatial resolution and a high throughput for inspecting an entire surface of an article during a surface inspection process.

More particularly, the surface inspection system preferably has a transporter arranged for transporting a workpiece along a material path and a rotator associated with the transporter and arranged for rotating a workpiece during translational travel along the material path. A scanner is positioned and arranged for scanning a surface of a workpiece during rotational and translational travel along the material path. The scanner preferably includes a light source arranged to generate a light beam therefrom and means positioned to receive the light beam and arranged for scanning the light beam along a predetermined scan path across a surface of the workpiece as the workpiece rotationally and translationally travels along the material path. A collector also is preferably arranged for collecting light reflected and scattered from the surface of the workpiece during rotational and translational travel along the material path.

A scanner is provided according to the present invention and is positioned and arranged to scan a surface of a workpiece during rotational and translational travel along a material path. The scanner preferably includes a light source, i.e., laser, arranged to generate a light beam therefrom and means positioned to receive the light beam and arranged for scanning the light beam along a predetermined, and preferably relatively narrow, scan path across a surface of the workpiece as the workpiece rotationally and translationally travels along the material path. The scanning means is preferably an acousto-optic deflector that preferably provides a relatively narrow scan path of less than about 0.1 radians that directionally corresponds to the translational path of travel of the workpiece.

A collector according to the present invention is also provided and preferably includes a light channel detector arranged for detecting light specularly reflected from the surface of a workpiece and a dark channel detector positioned adjacent the light channel detector for detecting light scattered from the surface of a workpiece. The dark channel detector preferably has a plurality of collectors positioned adjacent each other and arranged for collecting components of the scattered light at different respective predetermined angles from the surface of the workpiece and/or from the angle of light reflected from the surface of the workpiece. The plurality of collectors of the dark channel detector form segmented optics having at least two collectors positioned adjacent each other. The plurality of collectors are preferably a small angle collector arranged to collect light components scattered forwardly from the surface of the workpiece at a relatively small angle, a medium angle collector positioned adjacent the small angle collector and arranged to collect light components scattered substantially normal from the surface of the workpiece at a relatively medium angle, and a large angle collector positioned adjacent the medium angle detector and arranged to collect light components scattered backwardly from the surface of the workpiece at a relatively large angle. The dark channel detector further includes a small angle detector, a medium angle detector, and a large angle detector each respectively positioned in optical communication with a corresponding collector, and means electrically connected to the small, medium, and large angle detectors and responsive to electrical signals from the detectors for determining the presence of a particle on the surface of a workpiece.

When a particle or defect is detected, for example, the small angle collector is positioned to receive and collect forward scattering, the medium angle collector is positioned to receive and collect substantially normal scattering, and the large angle collector is positioned to receive and collect back scattering from the surface of the workpiece. The dark channel collector, more particularly, provides a surface inspection system according to the present invention with high sensitivity to more readily identify, classify, and/or provide a topography of the condition of the surface of an article or a workpiece, including particles, defects, scratches, or flaws in and on a surface of a workpiece Methods of inspecting a surface of an article or workpiece for defects are also provided according to the present invention. A method of inspecting a surface of a workpiece preferably includes rotatively and translationally transporting a workpiece along a material path and scanning a relatively narrow scan path of light across a surface of the workpiece as the workpiece travels along the material path. The step of rotatively and translationally transporting a workpiece along a material path preferably is synchronized with the step of scanning a surface of the workpiece so as to impart a substantially-shaped scan of the surface of the workpiece. Light specularly reflected from and light scattered from the surface of the workpiece preferably are separately collected. The collected scattered light preferably includes at least separately collecting light components scattered forwardly from the surface of the workpiece and collecting light components scattered backwardly from the surface of the workpiece. At least the speed of rotating, and preferably including the speed of translationally transporting, the workpiece during the scanning of the surface thereof may be varied so as to provide a substantially constant scanning speed of the surface of the workpiece. Also, the optical gain of the scanned light further may be varied during the scanning of the surface of the workpiece.

Another method of inspecting a surface of a workpiece preferably includes deflecting a light beam along a predetermined, i.e., relatively narrow, scan path and directing the deflected light beam from the scan path toward a surface of the workpiece, e.g., at a relatively low angle of incidence. The method preferably also includes imparting a rotational and translational scan of the workpiece so that the narrow scan path traverses the entire surface of the workpiece along a spiral path.

Yet another method of inspecting a surface of a workpiece to provide information about particles detected on a surface of a workpiece preferably includes detecting light reflected from the surface of a workpiece and detecting light scattered from the surface of a workpiece by a plurality of collectors at a plurality of predetermined scattering angles. At least two of the plurality of collectors positioned at the predetermined scattering angles preferably are respectively positioned to collect forwardly and backwardly scattered light from the surface of the workpiece. A particle or defect in or on the surface of the workpiece is identified responsive to light detected at a plurality of predetermined scattering angles.

A method of inspecting a surface of a workpiece according to the present invention further includes collecting light scattered from the surface of the workpiece at a first predetermined scattering angle arranged to collect forwardly scattered light, collecting light scattered from the surface of a workpiece at a second predetermined scattering angle arranged to collect substantially normal scattered light, and collecting light scattered from the surface of a workpiece at a third predetermined scattering angle arranged to collect backwardly scattered light.

Additionally, a method of inspecting a surface of a workpiece to provide information about particles, defects, or other surface characteristics in or on the surface the workpiece preferably includes collecting light scattered from the surface of a workpiece by a plurality of collectors arranged at a plurality of closely adjacent predetermined scattering angles so as to form signals representative of the collected light. The predetermined scattering angles are preferably arranged with respect to the surface of the workpiece so as to respectively collect at least forwardly and backwardly scattered light. These signals are then compared to predetermined data representative of dielectric constants of predetermined materials to identify a particle or a defect detected in or on the surface of the workpiece.

In addition to the above advantages, the surface inspection system and methods of the invention also provides high spatial resolution, a small field of view at the object plane which, in turn, provides improved edge detection performance and improved repeatability in the inspection process. Further, because the dark channel collector is arranged in a particular configuration having a plurality of detectors arranged at predetermined angles to the surface of the workpiece, the surface inspection system reduces interference signals, i.e., due to molecular scatter, in the detection of the reflected and scattered light from the surface of a workpiece.

BRIEF DESCRIPTION OF THE DRAWINGS

Other objects and advantages will appear as the description proceeds when taken in connection with the accompanying drawings, in which.

DETAILED DESCRIPTION

The present invention now will be described more fully hereinafter with reference to the accompanying drawings in which preferred embodiments of the invention are shown. This invention may, however, be embodied in many different forms and should not be construed as limited to the illustrated embodiments set forth herein; rather, these illustrated embodiments are provided so that this disclosure will be thorough and complete and will fully convey the scope of the invention to those skilled in the art. Like numbers refer to like elements throughout.

Figure 1:
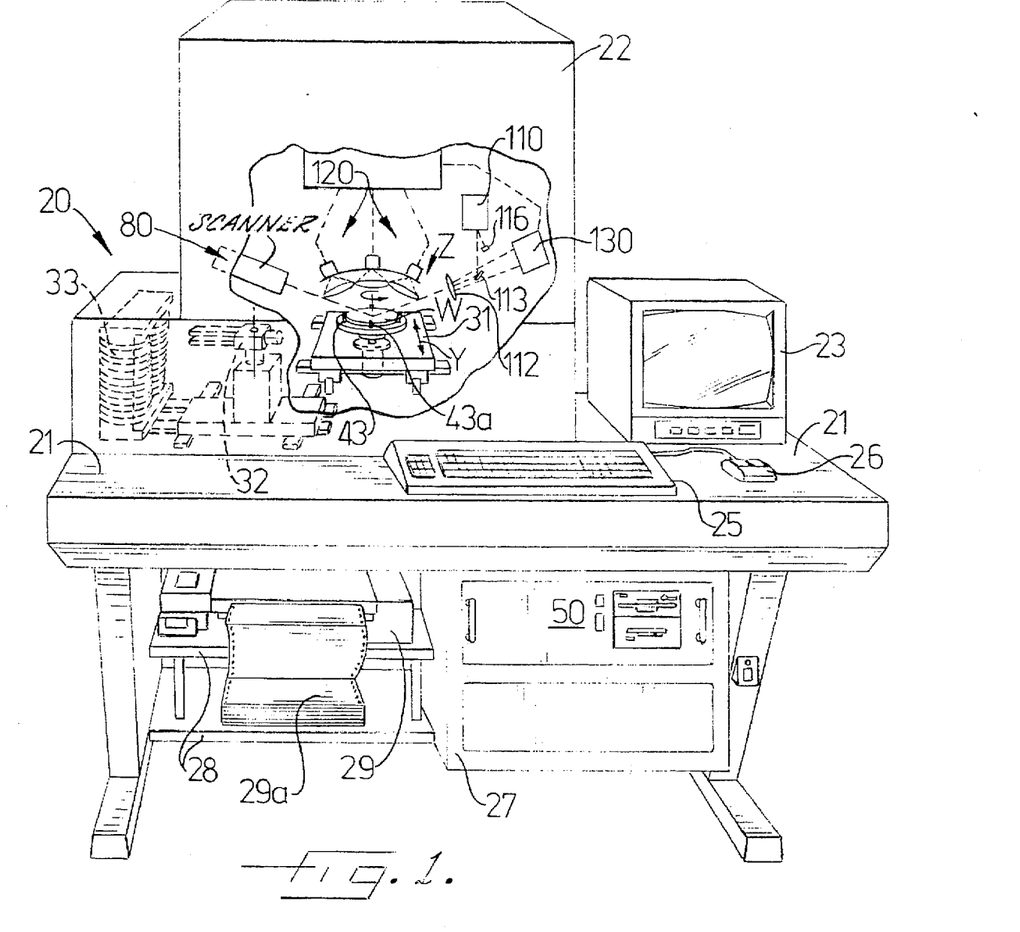
FIG. 1 illustrates a perspective view of a surface inspection system according to the present invention.

FIG. 1 illustrates a perspective view of a surface inspection system 20 for detecting particles, defects, flaws, and the like on a surface of a workpiece W or article, such as a silicon wafer, according to the present invention. Portions of the system 20 are broken away for clarity purposes and shown by phantom lines to illustrate various elements of the surface inspection system 20. The surface inspection system 20 of the invention is preferably used for inspecting the surface of unpatterned wafers W, both with and without deposited films. The system 20 preferably includes means for translationally transporting a workpiece W along a material path P, means associated with the translational transporting means for rotating the workpiece W as it travels along the material path P, means for scanning the surface S of the workpiece W during rotative and translational travel along the material path P, and means for collecting light reflected and scattered from the surface S of the workpiece W.

As illustrated in FIG. 1, the surface inspection system 20 is arranged as a workstation including a worktable 21. Positioned on the worktable 21 is a generally closed and substantially light proof housing 22, a video display 23, a keyboard 25, and a mouse 26. A cabinet 27 is suspended from the worktable for carrying a system controller 50. Adjacent the cabinet 27 is a shelf unit 28 for carrying a printer 29 and associated printing paper 29a. The housing 22 has been partially broken away to better illustrate the inspecting arrangement of the present invention. The inspection of the wafer W preferably is conducted in an inspection zone Z on an inspection table 31. A robotic wafer handling device 32 is located adjacent the inspection station 20 to load and unload wafers W from a cassette 33 onto the table 31. The cassette 33 holds a number of wafers W and is loaded into the cabinet 27 through a door (not shown). The handling of the wafers W inside the housing 22 is done automatically without contact by human hands to avoid contamination or smudges.

Figure 2:
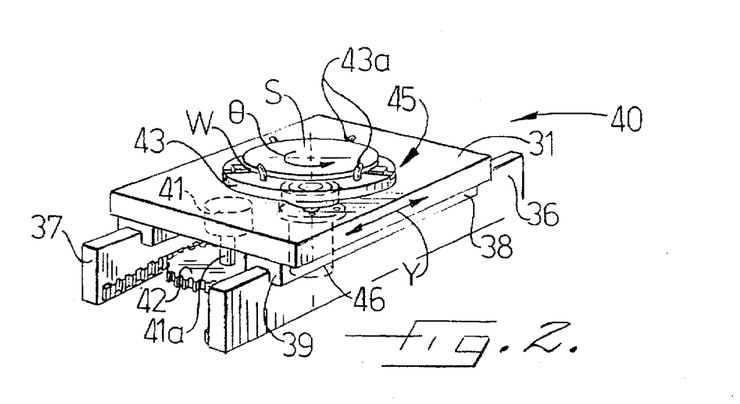
FIG. 2 illustrates a transporter of a surface inspection system according to the present invention arranged for rotatively and translationally transporting a workpiece along a material path.
Figure 3:
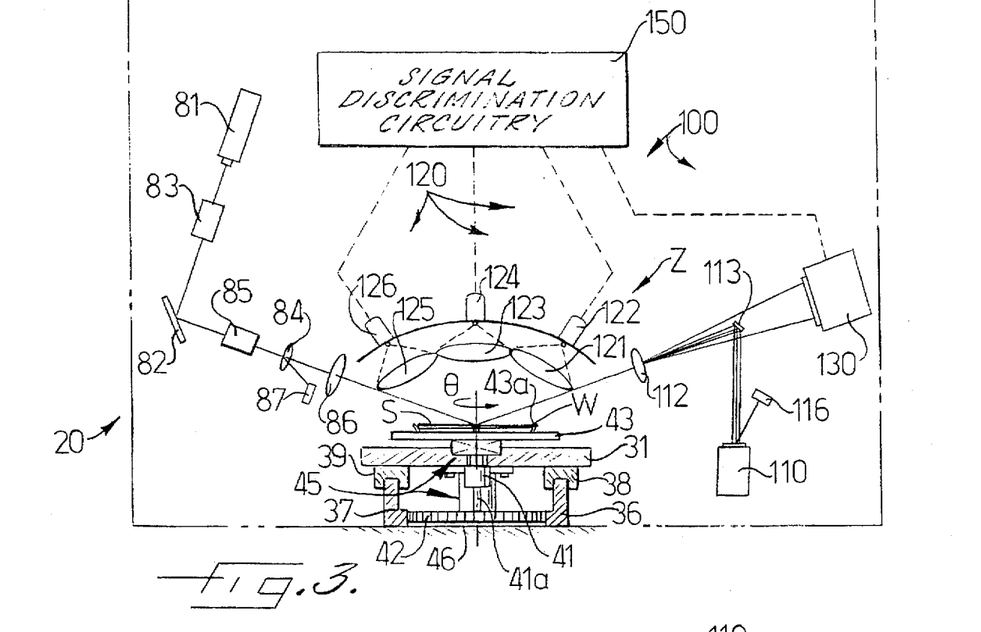
FIG. 3 schematically illustrates a side elevational view of a surface inspection system according to the present invention.

As best illustrated in FIGS. 1-3, the surface inspection system 20 preferably includes means for translationally transporting a workpiece W along a material path P. The means for transporting a workpiece W is illustrated as a transporter 40 arranged to translationally transport a workpiece W along a material path P and preferably through an inspection zone or area Z. The translational transporter 40, as illustrated, preferably includes a gear 42, a motor 41 including a shaft 41a arranged for rotating the gear 42, and guides 36, 37 having teeth formed integral therewith. The motor 41 and gear 42 mounted on the motor shaft 41a form a chuck for the system 50. The motor 41 of the chuck is preferably mounted to a stage member 43 having a plurality of flanges 43a extending upwardly therefrom which receives the workpiece W, i.e., silicon wafer, thereon along edges of the workpiece W as illustrated. This mounting technique for the workpiece W reduces smudges or other surface problems which may be associated with positioning the lower surface of the workpiece so as to abuttingly contact an upper surface of the stage member 43. The stage member 43 preferably is translationally transported along stage guide members 38, 39 secured to an underside thereof. Other translational and/or rotating means such as a piston and cylinder configuration mounted to the stage member and a motor for rotating the stage member as understood by those skilled in the art may also be used according to the invention.

Also, means for rotating a workpiece W, illustrated as a rotator 45, is associated with the transporter 40 and arranged to rotate a workpiece W during translational travel along the material path P. The rotator 45 as illustrated preferably includes a motor 46 mounted to an underside of the stage member for providing rotation of the wafer mounted thereon at a predetermined speed. The transporter 40 and the rotator 45 preferably are synchronized and arranged with a scanner 80 so as to form a spiral-shaped narrow angle scan ($\alpha$) across the surfaces of the workpiece during rotational and translational travel along the material path P.

As illustrated in FIGS. 1 and 3-5, a scanner 80 is positioned and arranged to scan a surfaces of a workpiece W during rotational and translational travel along the material path P. It will also be understood, however, by those skilled in the art that the scanner 80 may be arranged for rotational and/or translational movement while the workpiece W is stationary, or translationally or rotatively moved. Accordingly, the present invention includes a light source 81 arranged for generating a light beam B therefrom, means for receiving the light source and scanning a surface S of a workpiece W, i.e., a mirror 82, lenses 84, 86, deflector 85, and means for imparting a rotational and translational scan of the workpiece W, i.e., the transporter 40 and the rotator 45.

Figures 3A, 4:
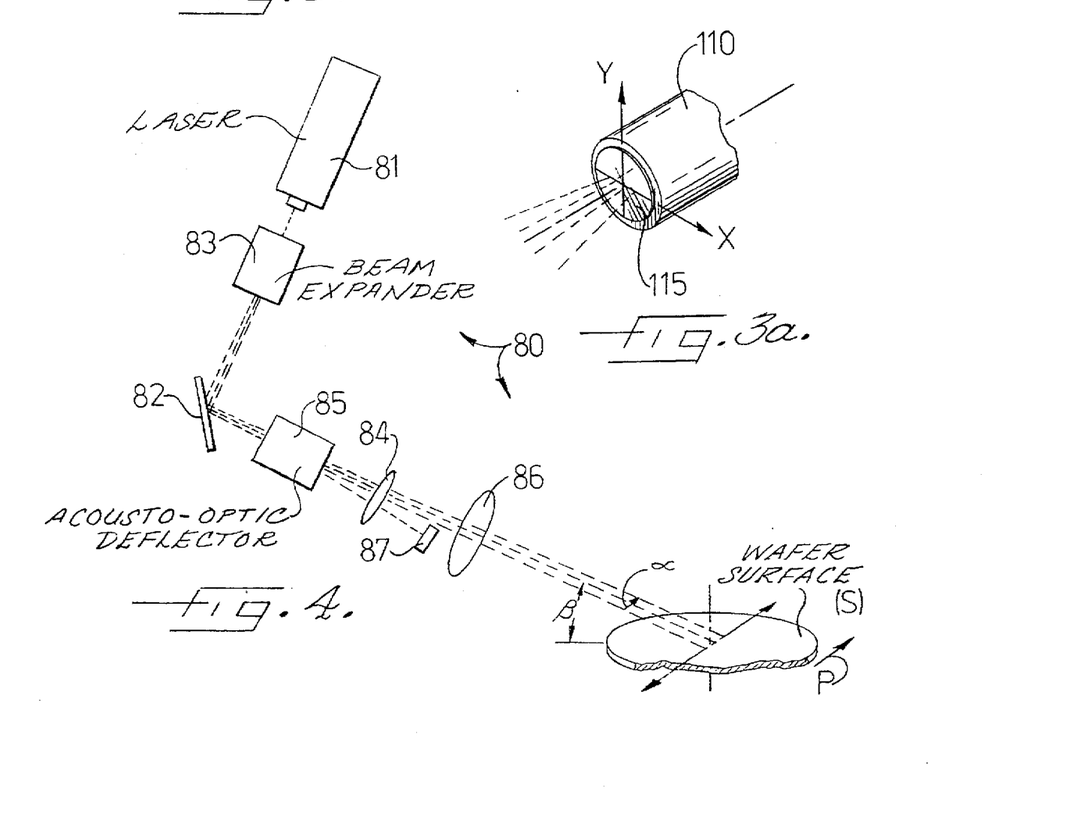
FIG. 3A illustrates a fragmentary view of a light channel detector of a surface inspection system according to the present invention.
FIG. 4 schematically illustrates a side elevational view of an optical scanning system of a surface inspection system according to the present invention.

The scanner 80 according to the invention preferably includes a light source 81, i.e., laser, arranged to generate a light beam B therefrom and means positioned to receive the light beam B and arranged for scanning the light beam B along a relatively narrow scan path (α) across a surface S of the workpiece W as the workpiece W rotationally and translationally travels along the material path P. The light source 81 is preferably a visible-light laser with a relatively short wavelength, such as Argon-Ion or solid state, as understood by those skilled in the art. The laser 81 is also preferably the combination of a laser with external optics as understood by those skilled in the art. The laser 81 preferably has a beam diameter of about 0.6 millimeters ("mm"). The scanner 80 which includes the associated optics illustrated, however, preferably is arranged to generate linear polarized, i.e., preferably P-polarized, light having a spot size which includes a full width, half-maximum of less than 0.1 millimeters. It will also be understood by those skilled in the art that S-polarized light or circular polarized light may also be generated and/or used according to the present invention.

In general, three important factors determine detection sensitivity for a surface inspection system 20 of the invention. The laser power, the laser wavelength, and the laser beam spot size. Laser power and spot size together determine the power density, which is directly proportional to scattered signal strength. For the surface inspection system 20 according to the present invention, the laser spot size is less than 60 microns, i.e., preferably in the range 25–40 microns, and, more particularly, is about 30 microns. This preferred laser spot size is about three times the pixel size, i.e. spatial resolution, which provides sufficient sampling of a surface inspection event and improved detection sensitivity. By decreasing the spot size, and assuming that gains, collection angles, and optical efficiencies are the same, significant improvement can be obtained in the detection limit, which is determined by the signal-to-noise ("S/N") ratio, of the surface inspection system 20. If the laser power is substantially increased, i.e., doubled, then the detection limit is significantly improved. If no change in the laser power occurs, however, optimizing the incident angle, polarization, and collection geometry can also improve the detection limit.

The scanning means preferably includes a deflector 85, as illustrated, positioned to receive the light beam B and arranged to deflect the light beam B along a relatively narrow scan path (α). The deflector 85 is preferably an acousto-optical (AO) deflector as illustrated, and the relatively narrow scan path (α) is preferably no greater than 0.1 radians and, more particularly, in the range of 0.025–0.040 radians. The scan path α preferably directionally corresponds to the path P of translational travel and, as best illustrated in FIG. 4, preferably is in a generally parallel direction therewith as illustrated by the arrows. The deflection is accomplished by exciting a crystal with high frequency sound waves, for example, which interact with the incident light wave in such a way to shift the light beam B and thereby change the angle of propagation. It will be understood that various frequencies of the crystal will responsively cause the light passing therethrough to be deflected at correspondingly various angles of propagation. If the frequency of the sound waves is swept in a sawtooth pattern, the laser beam B is scanned through an angle (α) proportional to the frequency. The AO deflector 85 preferably provides a constant scanning speed which, in turn, provides a consistent or a predetermined time response for particles or defects detected from an article surface.

Although the present invention is described with reference to an AO deflector 85, other means for providing narrow angle scans as understood by those skilled in the art, such as a galvanometer, a piezoelectric scanner, a resonant scanner, a rotating mirror, a scanning head, other electronic scanners, or the like, may also be used according to the present invention.

Also, a beam expander 82 is preferably positioned between the laser source 81 and the deflector 85 to expand the light beam B prior to entering the acousto-optical deflector 85. The beam expander 82 preferably provides means for more fully filling the active aperture of the deflector 85 to best utilize the scan angle of the deflector 85. Any expansion after or downstream from the deflector 85, for example, reduces the angle of deflection by the same factor as the beam diameter is increased. The practical beam diameter at the deflector 85 is limited by the required retrace time which is given by the following expression:

$$T=D/V_a$$

where D is the beam diameter and $V_a$ is the velocity of sound in a transducer positioned therein.

The scanner 80 also preferably includes means positionally aligned with the deflector 85 and arranged for directing the light beam from the narrow scan path (α) toward a surface S of a workpiece W at a relatively low angle of incidence (β) as the workpiece W rotatively and translationally travels along the material path P. Although the angle of incidence (β) may be substantially normal or less to the workpiece W depending on the particular application, the relatively low angle of incidence (β) is preferably greater than 45 degrees from normal to the article surface, i.e., less than 45 degrees from the surface of the workpiece W and, more particularly, is preferably in the range of 65–85 degrees from normal to the article surface.

The directing means is illustrated as a mirror 82 and a plurality of optical lenses 84, 86 arranged to direct the light beam B from the laser 81 toward the surface S of the workpiece W to be inspected. As the light beam B travels from the AO deflector 85, the beam B passes through a cylindrical lens 84 which preferably angularly orients the light beam B for a liner scan of the surface of the article during translational and rotational movement of the article through the inspection zone. A stop member 87 is positionally aligned with the cylindrical lens 84 positioned closely adjacent the AO deflector 85 to stop the relatively small portion of light which is not linearly oriented for the scan of the surface of the workpiece W. The optical lens 86 positioned after the cylindrical lens 84 is a focusing or f-theta lens, as understood by those skilled in the art, arranged for focusing the light beam on the surface of the workpiece W.

Figure 5:
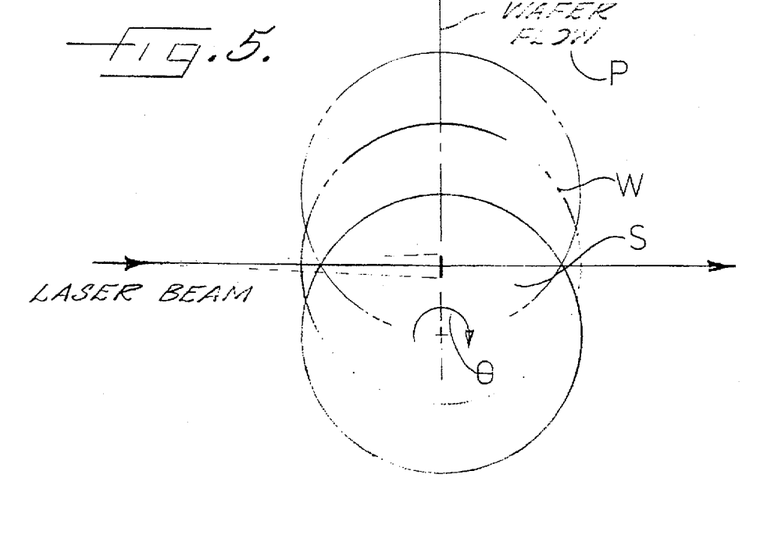
FIG. 5 schematically illustrates rotational and translational travel of a workpiece through an inspection area according to the present invention.

The scanner 80 according to the present invention preferably is arranged with respect to the transporter 40 and the rotator 45, which preferably are synchronized, so as to form a spiral-shaped narrow angle scan of the surface S of the workpiece W during rotational and translational travel along the material path P (see FIG. 5). The scanner 80 therefore scans the beam of light B in a radial direction θ with rotating motion and linear, lateral, or translational motion (Y) to implement a spiral scan pattern as best illustrated in FIG. 3.

The direction of the scan path α preferably corresponds to the direction of translational travel (Y) of the workpiece W. The narrow angle scan preferably begins at the outer radius of the rotating workpiece, i.e., wafer. The workpiece preferably is rotating at a predetermined speed, i.e., about 50 revolutions per minute ("rpm"). The stage member 43 upon which the workpiece W is mounted preferably moves synchronously with the rotation to create a smooth spiral. As the radius decreases, the rotational speed, as well as the translational speed, are gradually increased to keep the scan rate of the acousto-optical deflector 85 substantially constant. This scan process continues until the innermost five rotations at which a relatively constant rotational speed, i.e., about 200 rpm, is maintained. The predetermined rotational speed is determined to minimize the potential lateral or translational forces due to any system imbalances. The rotator 45 preferably includes means for varying the speed, i.e., variable speed motor 46, of rotating the workpiece during translational travel along the material path P during the scan of the surface S of the workpiece W. Likewise, the transporter 40 includes means for varying the speed, i.e., variable speed motor 41, of translationally transporting the workpiece during travel along the material path P during the scan of the surface S of the workpiece W.

Additionally, the light output power or optical gain of the light beam B may also be increased or decreased at various portions of the workpiece W which is being inspected for various surface characteristics, i.e., lowering optical gain along peripheral portions of the workpiece W. This varying of the light output power or optical gain can also assist in minimizing interferences caused by areas of increased surface roughness or other features affecting the ability of the system to detect particles or defects in or on the surface, as well as provide other system performance advantages. The surface inspection system 20 of the invention thereby provides high spatial resolution, high throughput, a small field of view at the object plane which, in turn, provides improved edge detection performance and improved repeatability in the inspection process.

As best illustrated in FIGS. 1, 3, 3A, and 6-7, means for collecting light from the surface of a workpiece is preferably a collector 100 having a light channel detector 110 arranged for detecting light specularly reflected from the surface S of a workpiece W and a dark channel detector 120 positioned adjacent the light channel detector 110 for detecting light scattered from the surface S of a workpiece W. The light channel detector 110 may be a PMT or a photodiode, but preferably, as understood by those skilled in the art, is a quadrant-cell device, i.e., detector, arranged for X-Y coordinate positioning detection so that deviation in the path of reflected light, i.e., during detection of a defect or particle, may be determined. Such quadrant-cell detectors are manufactured by Advanced Photonix, Inc., formerly Silicon Detector Corp., of Camarillo, Calif. Although a particular configuration is illustrated, it will be understood that various other rectangular or multiple cell, i.e., bi-cell, configurations may also be used according to the present invention.

Figure 6:
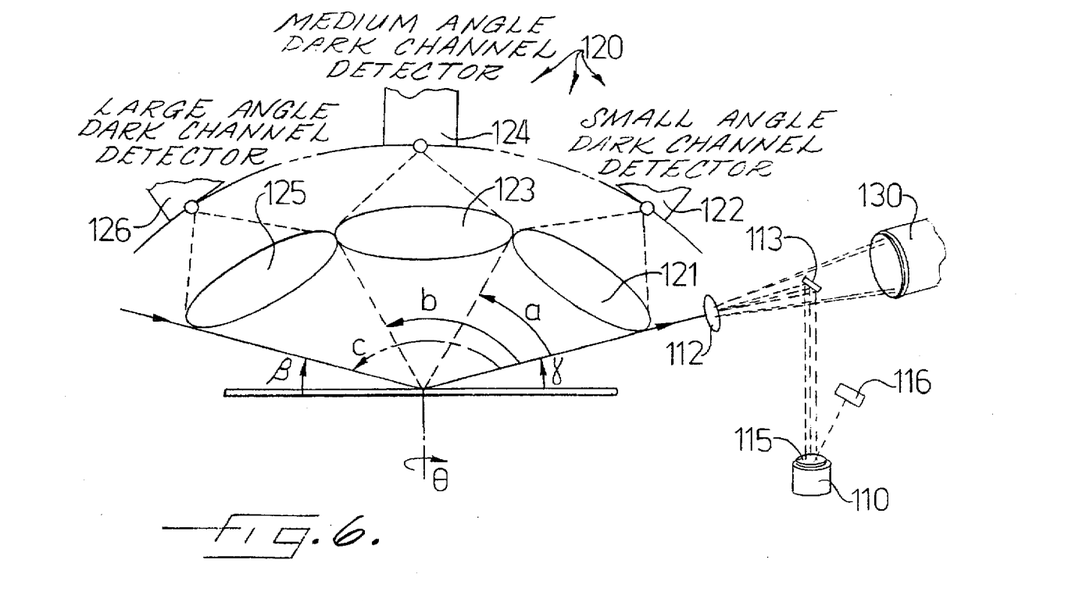
FIG. 6 schematically illustrates a collector of a surface inspection system having segmented optics for collecting light scattered from surface of a workpiece according to the present invention.

The dark channel detector 120 preferably includes a plurality of collectors 121, 123, 125 positioned closely adjacent each other and arranged for collecting components of the scattered light at different respective predetermined angles from the surface S of the workpiece W. The plurality of collectors 121, 123, 125 of the dark channel detector 120 form segmented optics having at least two collectors positioned adjacent each other. The plurality of collectors 121, 123, 125 as illustrated will be understood by those skilled in the art to be compound lenses, and other lens arrangements may also be used according to the present invention. The plurality of collectors 121, 123, 125 respectively include a small angle collector 121 arranged to collect light components scattered forwardly from the surface S of the workpiece W at a relatively small angle a, a medium angle collector 123 positioned closely adjacent the small angle collector 121 and arranged to collect light components scattered substantially normal from the surface S of the workpiece W at a relatively medium angle b, and a large angle collector 125 positioned closely adjacent the medium angle collector 123 and arranged to collect light components scattered backwardly from the surface S of the workpiece W at a relatively large angle c. The dark channel detector 120 further includes a small angle detector 122, a medium angle detector 124, and a large angle detector 126 each respectively positioned in optical communication with a corresponding collector 121, 123, 125, and means electrically connected to the small, medium, and large angle detectors 122, 124, 126 and responsive to electrical signals from said detectors for determining the presence of a particle on the surface S of a workpiece W.

The scratch detector 130 (FIG. 6) preferably is arranged to receive light which deviates from the reflected path illustrated. As the light is reflected from the surface of the workpiece W, it passes through a focusing lens 112 and strikes the surface of a reflective mirror 113. The mirror 113 orients the light toward the front surface 115 of the light collector 110 as illustrated. Light reflected from the front surface is dumped or stopped by a stop member 116. If a scratch, however, is detected in the surface of the workpiece W, significant portions of the reflected light as illustrated will deviate from the path directed toward the light collector 110 and will bypass the mirror 113 and strike the scratch detector 130, i.e., PMT. The determining means of the collector is preferably electronic signal discrimination circuitry 150, such as illustrated (see FIGS. 3 and 7) and understood by those skilled in the art, which receives signals representative of collected light from the dark channel detectors 122, 124, 126, 130.

As best illustrated in FIGS. 1, 3, and 6, the relative respective angles a, b, c of the plurality of collectors 121, 123, 125 are preferably determined with respect to the angle of reflection $\alpha$ of light from the surface S of the workpiece W and with respect to forward a, backward c, and substantially normal b light component scattering which occurs relative to the angle of incidence $\beta$ of the scan. For example, if the angle of incidence is relatively low, i.e., 15° from horizontal or −75° from normal, then the forward scattering or small angle a is preferably about +22° to 67°, the substantially normal scattering or medium angle is about −25° to +20°, and the backward scattering or large angle is about −72° to −27°. When a particle or defect is detected, for example, the small angle collector 121 is positioned to receive and collect forward scattering a, the medium angle collector 123 is positioned to receive and collect substantially normal scattering b, and the large angle collector 125 is positioned to receive and collect back scattering c from the surface of the workpiece with respect to the detected particle or defect, or the like. In the direction generally perpendicular to the plane of incidence, approximately 73° of total angle is captured in the above example. This is about 0.64 steridians of solid angle per segment or a total of about 1.92 steridians which is a substantial improvement over previous known detectors.

The dark channel collector 120 according to the present invention preferably analyzes the characteristics of surface S and particle scattering such as for use on polished wafers and various deposited films. When certain conditions, i.e., most related to allowable levels of surface roughness, are met, the distribution of light scattered from a surface (BRDF) can be expressed as:

$$BRDF = [16 \pi^2 \cos \beta_i \cos \beta_s Q \, S \, (f_x, f_y)]/\lambda^4$$

where $\beta_i$ is the incident angle, $\beta_s$ is the scattering angle, Q is the reflectance at the wavelength and polarization of incident light, S is the power spectral density characteristic of the surface roughness, $\lambda$ is the wavelength of incident light, $f_x$, $f_y$ are the spatial frequencies which, in turn, are expressed in terms of incident and scattering angles as follows:

$$f_x = (\sin \beta_s \cos \phi_s - \sin \beta_i)/\lambda$$

$$f_y = \sin \beta_s \sin \phi_s/\lambda.$$

In these equations, $\beta$ always refers to angles in the plane of incidence and $\phi$ represents azimuthal angles. The shape of the BRDF curve is defined by $S(f_x, f_y)$ and the cosine terms in the above equation which provide acceptable results given good power spectral density information. The magnitude of the curve is determined primarily by the reflectance Q.

The reflectance of the surface of the article and a particle or defect detected thereon is dependent on the dielectric constant of the material or particle inspected, i.e., silicon, aluminum. Also, the reflectance of a material or particle illuminated with P polarized light, preferable according to the present invention, will have different characteristics than a material or particle illuminated with S polarized light. The reflectance of a dielectric illuminated with P polarized light is zero at a certain angle, i.e., Brewster's angle, and is a function of the index of refraction (n) as follows:

$$\beta_b = \tan^{-1} n.$$

Metals and other absorbing materials, for example, exhibit curves with similar shapes; however, the reflectance for P polarization reaches a non-zero minimum. The angle where this non-zero minimum occurs may be referred to as a pseudo-Brewster's angle or alternately as the principal angle. The principal angle is dependent on the complex dielectric constant (n'=n–ik) and can be found by evaluating the following expression on an iterative basis:

$$(n^2+k^2)^{1/2} = \sin^2 \beta_p/\cos \beta_p.$$

For example, although aluminum and silicon are different, aluminum being a strong absorber and silicon exhibiting dielectric characteristics with a high index, the principal angle of both materials is close to the same, i.e., about 78° (aluminum 78.1°, silicon 77.8°). Almost all other materials of interest will have indices no larger than aluminum or silicon and therefore will have principal angles equal to or less than about 78°, e.g., silicon dioxide has an index of refraction of about 1.65 which equates to a principal angle of about 58.8°. The characteristics of dielectric films are also dependent on the substrate and film thickness, and the reflectance curve may exhibit minima at several angles.

Data representative of these various values from the BRDF curve, the indices of refraction, and dielectric constants may be used to determine particle or defect identification information for the surface inspection system 50. A relative signal to noise ratio for determining the scattering angle may be obtained by taking the particle response and dividing by the square root of the BRDF. This provides an equivalent signal to noise ratio in the limit where the dominant source of noise is the Poisson fluctuation of the "haze" signal as understood by those skilled in the art. This comparison of the resulting angles of collected light from the dark channel collector 120, i.e., scattered light, is compared to known characteristic data such as in a data table to assist with this determination and then classify the particle or defect accordingly. These comparative steps are preferably performed according to predetermined command signals, i.e., a software program, resident in the structural hardware or on a stored disk or the like as understood by those skilled in the art.

Figure 7:
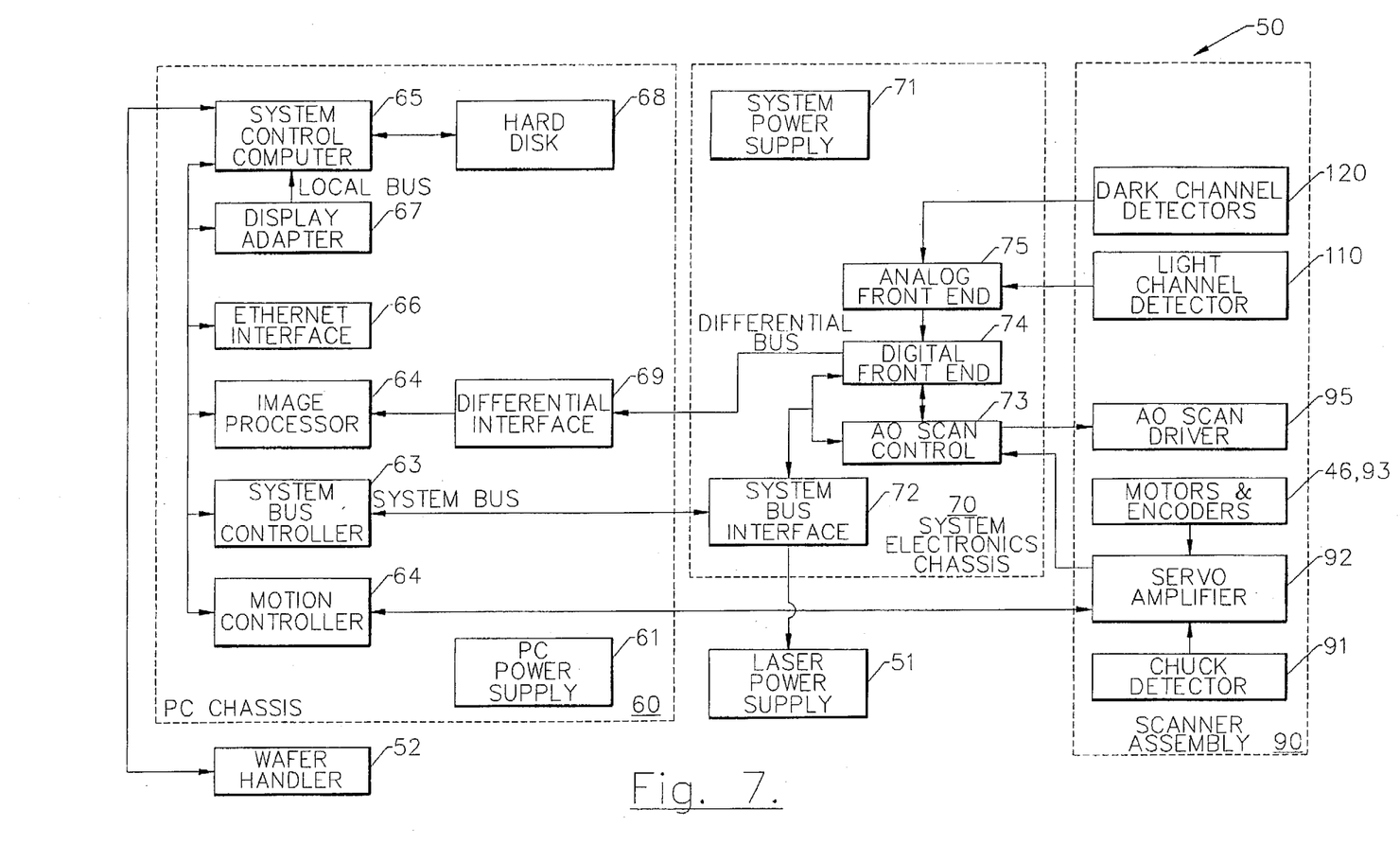
FIG. 7 schematically illustrates a system controller of a surface inspection system according to the present invention.

As best illustrated in the perspective view of FIG. 1 and the schematic view of FIG. 7, the surface inspection system 20 preferably is computer controlled. The system controller 50 operates the inspection system 20 under the supervision and direction of a human operator, stores and retrieves data generated by the system 20, and performs data analysis preferably responsive to predetermined commands. The scanner assembly portion 90 illustrated cooperates with the scanner 80 and includes a chuck detector 91 which transmits a position to a servo-amplifier 91. The relative position of the article being inspected is communicated to the system 50 via motors 41, 46 and encoders 93 mounted thereto. The position data is transmitted to the AO scan control 73 which preferably forms a portion of the system electronics chassis 70 and which responsively drives the AO deflector 85 via a AO scan driver 95.

The system electronics chassis 70 includes a system power supply 71 and receives signals from the dark channel detectors 120 and the light channel detector 110 respectively representative of the scattered and the specularly reflected light. As understood by those skilled in the art, these data signals are conventionally electrically communicated in an analog format to analog front end electronics 75 and are converted to digital format by digital front end electronics 74 or the like. The digital front end electronics 74 also cooperates with the AO scan control 73, the system bus interface 72, and the differential interface 69, i.e., differential bus, of the personal computer ("PC") chassis 60. The system bus interface 72 also communicates with a laser power supply 51 of the surface inspection system 50.

The PC chassis 60 includes a PC power supply 61 arranged for supplying power to the PC. The PC chassis 60 also has a motion controller 64 which responsively communicates with the servo amplifier 92 of the scanner assembly 90 and a system control computer 65, i.e., microprocessor, or controller. The system control computer 65 preferably electrically communicates with a wafer handler 52 for responsively sending and receiving predetermined command signals for mounting and handling the article or wafer being inspected as set forth above. The system control computer 65 also preferably communicates with a hard disk drive 68, a display adapter 67 arranged to communicate with the display, and an ethernet interface 66 arranged for network or other system 50 communication. An image processor 64 electrically communicates with the differential interface 69 and the system control computer 65 for processing the image of the surface of the inspected article and/or defects, flaws, undulations, or particles thereon. The surface inspection system 50 as illustrated in FIG. 7 and as understood by those skilled in the art preferably is formed of a combination of software and hardware which forms these various components, or combinations thereof, of the system 50.

As illustrated in FIGS. 1–7, methods of inspecting a surface S of an article or workpiece W for defects are also provided according to the present invention. A method of inspecting a surface S of a workpiece W preferably includes rotatively and translationally transporting a workpiece W along a material path P and scanning a relatively narrow scan path $\alpha$ of light across a surface of the workpiece W as the workpiece W travels along the material path P. The step of rotatively and translationally transporting a workpiece along a material path preferably is synchronized with the step of scanning a surface of the workpiece so as to impart a substantially-shaped scan of the surface of the workpiece.

Light specularly reflected from and light scattered from the surface S of the workpiece W preferably are separately collected. The collected scattered light preferably includes at least separately collecting light components scattered forwardly from the surface S of the workpiece W and collecting light components scattered backwardly from the surface S of the workpiece W. At least the speed of rotating, and preferably including the speed of translationally transporting, the workpiece during the scanning of the surface thereof may be varied so as to provide a substantially constant scanning speed of the surface S of the workpiece W. Also, the optical gain of the scanned light further may be varied during the scanning of the surface of the workpiece.

Another method of inspecting a surface S of a workpiece W preferably includes deflecting a light beam B along a predetermined, i.e., relatively narrow, scan path α and directing the deflected light beam B from the scan path α toward a surface S of the workpiece W, e.g., at a relatively low angle of incidence. The method preferably also includes imparting a rotational and translational scan of the workpiece W so that the narrow scan path traverses the entire surface 8 of the workpiece W along a spiral path.

Yet another method of inspecting a surface S of a workpiece W to provide information about particles detected on a surface of a workpiece W preferably includes detecting light reflected from the surface S of a workpiece W and detecting light scattered from the surface S of a workpiece W by a plurality of collectors 121, 123, 125 at a plurality of predetermined scattering angles a, b, c. At least two of the plurality of collectors 121, 125 positioned at the predetermined scattering angles preferably are respectively positioned to collect forwardly and backwardly scattered light from the surface S of the workpiece W. A particle or defect in or on the surface S of the workpiece W is identified responsive to light detected at a plurality of predetermined scattering angles.

A method of inspecting a surface S of a workpiece W according to the present invention further includes collecting light scattered from the surface S of the workpiece W at a first predetermined scattering angle arranged to collect forwardly scattered light, collecting light scattered from the surface of a workpiece at a second predetermined scattering angle arranged to collect substantially normal scattered light, and collecting light scattered from the surface of a workpiece at a third predetermined scattering angle arranged to collect backwardly scattered light.

Additionally, a method of inspecting a surface S of a workpiece W to provide information about particles, defects, or other surface characteristics in or on the surface the workpiece preferably includes collecting light scattered from the surface of a workpiece W by a plurality of collectors 121, 123, 125 arranged at a plurality of closely adjacent predetermined scattering angles a, b, c so as to form signals representative of the collected light. The predetermined scattering angles are preferably arranged with respect to the surface of the workpiece so as to respectively collect at least forwardly and backwardly scattered light. These signals are then compared to predetermined data representative of dielectric constants of predetermined materials to identify a particle or a defect detected in or on the surface of the workpiece W.

In the drawings and specification, there have been disclosed typical preferred embodiments of the invention, and, although specific terms are employed, these terms are used in a descriptive sense only and not for purposes of limitation. The invention has been described in considerable detail with specific reference to various illustrated embodiments. It will be apparent, however, that various modifications and changes can be made within the spirit and scope of the invention as described in the foregoing specification and defined in the appended claims.

That which is claimed:

1. A surface inspection system for detecting particles or defects on a surface of a workpiece, the surface inspection system comprising:

means for translationally transporting a workpiece along a material path;

means associated with said transporting means for rotating a workpiece during translational travel along the material path;

a scanner positioned and arranged to scan a surface of a workpiece during rotational and translational travel along the material path, said scanner including a light source arranged to generate a light beam therefrom and means positioned to receive the light beam and arranged for scanning the light beam along a predetermined scan path across a surface of the workpiece as the workpiece rotationally and translationally travels along the material path; and a collector arranged for collecting light reflected and scattered from the surface of the workpiece during rotational and translational travel along the material path, said collector comprising:

a light channel detector arranged for detecting light specularly reflected from the surface of a workpiece; and a dark channel detector positioned adjacent said light channel detector for detecting light scattered from the surface of a workpiece, said dark channel detector including a plurality of collectors positioned closely adjacent each other and arranged for collecting components of the scattered light at different respective predetermined angles from the surface of the workpiece.

2. A surface inspection system as defined by claim 1, wherein said translational transporting means and said rotating means are synchronized and arranged with said scanner so as to form a substantially spiral-shaped angle scan of the surface of the workpiece during rotational and translational travel along the material path.

3. A surface inspection system as defined by claim 2, wherein the predetermined scan path comprises a relatively narrow scan path of no greater than 0.1 radians along the surface of the workpiece.

4. A surface inspection system as defined by claim 2, wherein the predetermined scan path comprises a relatively narrow scan path in a range between about 0.025 to 0.040 radians.

5. A surface inspection system as defined by claim 1, wherein said scanning means comprises a deflector arranged to repetitively deflect the light beam along a predetermined narrow scan path along the surface of the workpiece.

6. A surface inspection system as defined by claim 1, wherein said plurality of collectors of said dark channel detector comprises a small angle collector arranged to collect light components scattered forwardly from the surface of the workpiece at a relatively small angle, a medium angle collector positioned adjacent said small angle collector and arranged to collect light components scattered substantially normal from the surface of the workpiece at a relatively medium angle, and a large angle collector positioned adjacent said medium angle collector and arranged to collect light components scattered backwardly from the surface of the workpiece at a relatively large angle, and wherein said dark channel detector further includes a small angle detector, a medium angle detector, and a large angle detector each respectively positioned in optical communication with a corresponding collector for detecting collected light, and means electrically connected to said small, medium, and large angle detectors and responsive to electrical signals from said detectors for determining the presence of a particle on the surface of the workpiece.

7. A surface inspection system for detecting particles or defects on a surface of a workpiece, the surface inspection system comprising:

a transporter arranged to translationally transport a workpiece along a material path;

a rotator associated with said transporter and arranged to rotate a workpiece during translational travel along the material path;

a scanner positioned and arranged to scan a surface of a workpiece during rotational and translational travel along the material path, said scanner including a laser source arranged to generate a laser light beam therefrom and a deflector positioned to receive the light beam and arranged to deflect the light beam along a relatively narrow scan path toward a surface of the workpiece as the workpiece rotatively and translationally travels along the material path;

a light channel detector arranged for detecting light specularly reflected from the surface of a workpiece; and a dark channel detector positioned adjacent said light channel detector for detecting light scattered from the surface of a workpiece, said dark channel detector including a plurality of collectors positioned adjacent each other and arranged for collecting components of the scattered light at different respective predetermined angles from the surface of the workpiece.

8. A surface inspection system as defined by claim 7, wherein said transporter and said rotator are synchronized and arranged with said scanner so as to form a spiral-shaped narrow angle scan of the surface of the workpiece during rotational and translational travel along the material path.

9. A surface inspection system as defined by claim 8, wherein the rotator includes means for varying the speed of rotating the workpiece during translational travel along the material path during the scan of the surface of the workpiece so as to provide a substantially constant scanning speed of the surface of the workpiece.

10. A surface inspection system as defined by claim 8, wherein the relatively narrow scan path along the surface of the workpiece is no greater than 0.1 radians.

11. A surface inspection system as defined by claim 10, wherein said deflector is arranged to repetitively deflect the light beam along a predetermined narrow scan path along the surface of the workpiece, and wherein said scanner further includes means for directing the light beam from the narrow scan path toward a surface of the workpiece at a relatively low angle of incidence as the workpiece rotatively and translationally travels along the material path.

12. A surface inspection system as defined by claim 11, wherein the relatively low angle of incidence is greater than 45 degrees from normal to the workpiece.

13. A surface inspection system as defined by claim 12, wherein said plurality of collectors of said dark channel detector comprises a small angle collector arranged to collect light components scattered forwardly from the surface of the workpiece at a relatively small angle, a medium angle collector positioned adjacent said small angle collector and arranged to collect light components scattered substantially normal from the surface of the workpiece at a relatively medium angle, and a large angle collector positioned adjacent said medium angle collector and arranged to collect light components scattered backwardly from the surface of the workpiece at a relatively large angle, and wherein said dark channel detector further includes a small angle detector, a medium angle detector, and a large angle detector each respectively positioned in optical communication with a corresponding collector for detecting collected light, and means electrically connected to said small, medium, and large angle detectors and responsive to electrical signals from said detectors for determining the presence of a particle on the surface of the workpiece.

14. A surface inspection system as defined by claim 8, wherein the relatively narrow scan path along the surface of the workpiece is in a range between about 0.025 to 0.040 radians.

15. A surface inspection system for detecting particles or defects on a surface of a workpiece, the surface inspection system comprising:

a transporter arranged to translationally transport a workpiece along a material path;

a rotator associated with said transporter and arranged to rotate a workpiece during translational travel along the material path;

a scanner positioned and arranged to scan a surface of a workpiece during rotational and translational travel along the material path, said scanner including a laser source arranged to generate a laser light beam therefrom, a deflector positioned to receive the light beam and arranged to deflect the light beam along a relatively narrow scan path, the relatively narrow scan path being no greater than 0.1 radians and directionally corresponding to the translational travel of the workpiece, and means positionally aligned with said deflector and arranged for directing the light beam from the narrow scan path toward a surface of a workpiece at a relatively low angle of incidence as a workpiece rotatively and translationally travels along the material path;

a light channel detector arranged for detecting light specularly reflected from the surface of a workpiece; and a dark channel detector positioned adjacent said light channel detector for detecting light scattered from the surface of a workpiece, said dark channel detector including a plurality of collectors positioned adjacent each other and at different respective predetermined angles from the surface of the workpiece.

16. A surface inspection system as defined by claim 15, wherein said transporter and said rotator are synchronized and arranged with said scanner so as to form a spiral-shaped narrow angle scan of the surface of the workpiece during rotational and translational travel along the material path.

17. A surface inspection system as defined by claim 16, wherein the rotator includes means for varying the speed of rotating the workpiece during translational travel along the material path and the transporter includes means for varying the speed of translationally transporting the workpiece along the material path during the scan of the surface of the workpiece so as to provide a substantially constant scanning speed of the surface of the workpiece.

18. A surface inspection system as defined by claim 17, wherein the relatively low angle of incidence is greater than 45 degrees from normal to the workpiece.

19. A surface inspection system as defined by claim 18, wherein said plurality of collectors of said dark channel detector comprises a small angle collector arranged to collect light components scattered forwardly from the surface of the workpiece at a relatively small angle, a medium angle collector positioned adjacent said small angle collector and arranged to collect light components scattered substantially normal from the surface of the workpiece at a relatively medium angle, and a large angle collector positioned adjacent said medium angle collector and arranged to collect light components scattered backwardly from the surface of the workpiece at a relatively large angle, and wherein said dark channel detector further includes a small angle detector, a medium angle detector, and a large angle detector each respectively positioned in optical communication with a corresponding collector for detecting collected light, and means electrically connected to said small, medium, and large angle detectors and responsive to electrical signals from said detectors for determining the presence of a particle on the surface of the workpiece.

20. A surface inspection system as defined by claim 19, wherein said directing means includes a mirror and a plurality of optical lenses positioned between said laser source and the material path and arranged to direct the light beam toward the surface of the workpiece to be inspected.

21. A surface inspection system arranged for scanning a surface of a workpiece, the surface inspection system comprising:

a light source arranged to generate a light beam therefrom;

means for receiving the light beam and scanning a relatively narrow scan path toward a surface of a workpiece; and means for imparting a rotational and translational scan of the workpiece, and means for varying the speed of rotating the workpiece during translational travel along the material path during the scan of the surface of the workpiece so as to provide a substantially constant scanning speed of the surface of the workpiece.

22. A surface inspection system as defined by claim 21, wherein the relatively narrow scan path along the surface of the workpiece is no greater than 0.1 radians.

23. A surface inspection system as defined by claim 22, wherein said scanning means comprises a deflector arranged to repetitively deflect the light beam along a predetermined narrow scan path along the surface of the workpiece.

24. A surface inspection system as defined by claim 22, further comprising means positionally aligned with said scanning means for directing the light beam toward the surface of the workpiece at a relatively low angle of incidence, said directing means including a mirror and a plurality of optical lenses.

25. A surface inspection system as defined by claim 21, wherein the relatively narrow scan path is in a range between about 0.025 to 0.040 radians.

26. An optical scanner arranged for detecting particles or defects on a surface of a workpiece, the optical scanner comprising:

a laser arranged to generate a laser light beam therefrom;

an acousto-optical deflector arranged to receive the light beam and to deflect the light beam along a relatively narrow scan path, the relatively narrow scan path being no greater than 0.1 radians;

means associated with said laser and said acousto-optical deflector for directing the light beam toward a surface of a workpiece at a relatively low angle of incidence as the workpiece rotatively and translationally travels along a material path, said directing means including a mirror and a plurality of optical lenses arranged to direct the light beam toward the surface of the workpiece to be inspected;

a light channel detector arranged for detecting light specularly reflected from the surface of a workpiece; and a dark channel detector arranged for detecting light scattered from the surface of a workpiece, said dark channel detector including a plurality of collectors positioned closely adjacent each other and arranged for collecting components of the scattered light at different respective predetermined angles from the surface of the workpiece.

27. An optical collector for collecting light reflected from a surface of a workpiece and for providing information about particles detected on a surface of a workpiece, the optical collector comprising dark channel detection means for detecting light scattered from a surface of a workpiece, said dark channel detection means including a plurality of collectors positioned adjacent each other and arranged for collecting components of the scattered light at different respective predetermined angles from the surface of the workpiece, said plurality of collectors including at least a collector arranged for collecting forwardly scattered light from the surface of the workpiece and a collector arranged for collecting backwardly scattered light from the surface of the workpiece.

28. An optical collector as defined by claim 27, wherein said plurality of collectors of said dark channel detector comprises a small angle collector arranged to collect light components scattered forwardly from the surface of the workpiece at a relatively small angle, a medium angle collector positioned adjacent said small angle collector and arranged to collect light components scattered substantially normal from the surface of the workpiece at a relatively medium angle, and a large angle collector positioned adjacent said medium angle collector and arranged to collect light components scattered backwardly from the surface of the workpiece at a relatively large angle, and wherein said dark channel detector further includes a small angle detector, a medium angle detector, and a large angle detector each respectively positioned in optical communication with a corresponding collector for detecting collected light, and means electrically connected to said small, medium, and large angle detectors and responsive to electrical signals from said detectors for determining the presence of a particle on the surface of the workpiece.

29. An optical collector arranged for collecting light reflected from a surface of a workpiece and for providing information about particles detected on a surface of a workpiece, the optical collector comprising:

a light channel detector arranged to detect light specularly reflected from the surface of a workpiece; and a dark channel detector positioned adjacent said light channel detector to detect light scattered from the surface of a workpiece, said dark channel detector including a small angle collector arranged for collecting light components forwardly scattered from the surface of the workpiece at a relatively small angle, a medium angle collector positioned closely adjacent said small angle collector and arranged for collecting light components scattered substantially normal from the surface of the workpiece at a relatively medium angle, and a large angle collector positioned closely adjacent said medium angle detector and arranged for collecting light components scattered backwardly from the surface of the workpiece at a relatively large angle, a small angle detector, a medium angle detector, and a large angle detector each respectively positioned in optical communication with a corresponding collector for respectively detecting the collected light, and a particle classifier electrically connected to said small, medium, and large angle detectors and responsive to electrical signals from said detectors to determine the presence of a particle on the surface of a workpiece.

30. An optical collector as defined by claim 29, wherein said dark channel collector further comprises a scratch detector positioned adjacent said light detector and said small angle detector for detecting a scratch in the surface of a workpiece.

31. A method of inspecting a surface of a workpiece comprising:
   rotatively and translationally transporting a workpiece along a material path;
   scanning a relatively narrow scan path of light across a surface of the workpiece as the workpiece travels along the material path; and
   separately collecting light specularly reflected from and light scattered from the surface of the workpiece, the collected scattered light including at least light components scattered forwardly and light components scattered backwardly from the surface of the workpiece.

32. A method as defined by claim 31, wherein the step of rotatively and translationally transporting a workpiece along a material path is synchronized with the step of scanning of a surface of the workpiece so as to impart a substantially spiral-shaped scan of the surface of the workpiece.

33. A method of inspecting a surface of a workpiece comprising:
   rotatively and translationally transporting a workpiece along a material path;
   scanning a relatively narrow scan path of light across a surface of the workpiece as the workpiece travels along the material path; and
   varying the speed of rotating and the speed of translationally transporting the workpiece during the scanning of the surface thereof so as to provide a substantially constant scanning speed of the surface of the workpiece.

34. A method as defined by claim 32, further comprising varying the optical gain of the scanned light during the scanning of the surface of the workpiece.

35. A method of inspecting a surface of a workpiece comprising:
   translationally transporting a workpiece along a material path at a predetermined speed;
   rotating the workpiece during translational travel along the material path at a predetermined speed;
   scanning a path of light across a surface of the workpiece as the workpiece travels along the material path; and
   varying at least the speed of rotating the workpiece during the scanning of the surface thereof so as to provide a substantially constant scanning speed of the surface of the workpiece.

36. A method as defined by claim 35, wherein the step of scanning a path of light across a surface of a workpiece comprises a relatively narrow angle scan, and wherein the step of varying at least the speed of rotating the workpiece further comprises varying the speed of translationally transporting the workpiece during the scanning of the surface thereof.

37. A method of inspecting a surface of a workpiece comprising:
   deflecting a light beam along a relatively narrow scan path; and
   directing the deflected light beam from the narrow scan path at a relatively low angle of incidence toward a surface of the workpiece; and
   imparting a rotational and translational scan of the workpiece so that the narrow scan path traverses the entire surface of the workpiece along a spiral path; and
   varying the speed of rotating and the speed of translation of the workpiece during the scanning of the surface thereof so as to provide a substantially constant scanning speed of the surface of the workpiece.

38. A method of inspecting a surface of a workpiece to provide information about particles detected on a surface of a workpiece, the method comprising:
   detecting light reflected from the surface of a workpiece; and
   detecting light scattered from the surface of a workpiece by a plurality of collectors arranged at a plurality of closely adjacent predetermined scattering angles, at least two of the plurality of collectors at the predetermined scattering angles being respectively positioned to collect forwardly and backwardly scattered light from the surface of the workpiece.

39. A method as defined by claim 38, wherein the plurality of collectors further comprises a collector positioned to collect substantially normal scattered light from the surface of the workpiece.

40. A method as defined by claim 38, further comprising identifying a defect in or on a surface of a workpiece responsive to light detected at a plurality of predetermined scattering angles.

41. A method of inspecting a surface of a workpiece to provide information about particles detected on a surface of a workpiece, the method comprising:
   collecting light scattered from the surface of a workpiece at a first predetermined scattering angle arranged to collect forwardly scattered light;
   collecting light scattered from the surface of a workpiece at a second predetermined scattering angle arranged to collect substantially normal scattered light; and
   collecting light scattered from the surface of a workpiece at a third predetermined scattering angle arranged to collect backwardly scattered light.

42. A method of inspecting a surface of a workpiece to provide information about particles detected on a surface of a workpiece, the method comprising:
   collecting light scattered from the surface of a workpiece by a plurality of collectors arranged at a plurality of closely adjacent predetermined scattering angles so as to form signals representative of the collected light, the predetermined scattering angles being arranged with respect to the surface of the workpiece so as to respectively collect at least forwardly and backwardly scattered light; and
   comparing signals representative of the collected light with predetermined data representative of dielectric constants of predetermined materials to identify a detected particle or defect on the surface of the workpiece.

* * * * *